United States Patent [19]
Huth et al.

[11] Patent Number: 6,143,733
[45] Date of Patent: *Nov. 7, 2000

[54] QUINOXALINEDIONE DERIVATIVES, THEIR PRODUCTION AND USE IN PHARMACEUTICAL AGENTS

[75] Inventors: Andreas Huth; Martin Krüger; Eckhard Ottow; Dieter Seidelmann; Graham H Jones; Herbert Schneider; Lechoslaw Turski, all of Berlin, Germany

[73] Assignee: Schering Aktiengesellschaft, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/817,771

[22] PCT Filed: Oct. 25, 1995

[86] PCT No.: PCT/DE95/01517

§ 371 Date: May 29, 1997

§ 102(e) Date: May 29, 1997

[87] PCT Pub. No.: WO96/12724

PCT Pub. Date: May 2, 1996

[30] Foreign Application Priority Data

Oct. 25, 1994 [DE] Germany .............................. 44 39 492

[51] Int. Cl.[7] ...................... A61K 31/498; A61K 31/675; C07F 9/6509; C07D 241/44
[52] U.S. Cl. ............................ 514/85; 514/249; 544/337; 544/354
[58] Field of Search ..................................... 544/337, 354; 514/249, 85

[56] References Cited

U.S. PATENT DOCUMENTS 5,166,155  11/1992  Jorgensen et al. ....................... 514/249
5,714,489   2/1998  Lubisch et al. .......................... 514/249

FOREIGN PATENT DOCUMENTS

93/08173  4/1993  WIPO .
94/25469  11/1994  WIPO .

OTHER PUBLICATIONS

Shishikura et al, *Chemical Abstracts*, vol. 125, No. 114689, (1996).
Epperson et al, *Bioorganic & Medicinal Chemistry Letters*, 3, p. 2801–2804, (1993).

*Primary Examiner*—Emily Bernhardt
*Attorney, Agent, or Firm*—Millen, White, Zelano & Branigan, P.C.

[57] ABSTRACT

Quinoxalinedione derivatives (I)

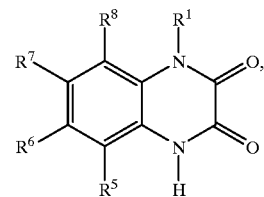

as well as their production and use in pharmaceutical agents are described.

4 Claims, No Drawings

QUINOXALINEDIONE DERIVATIVES, THEIR PRODUCTION AND USE IN PHARMACEUTICAL AGENTS

The invention relates to quinoxalinedione derivatives, their production and use in pharmaceutical agents.

It is known that quinoxaline derivatives have an affinity to the quisqualate receptors and, because of the affinity, are suitable as pharmaceutical agents for the treatment of diseases of the central nervous system.

The compounds according to the invention have formula I

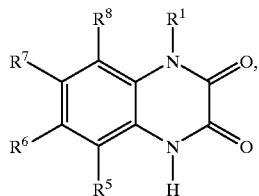

(I)

in which
$R^1$ means $-(CH_2)_n-CR^2H-(CH_2)_m-Z$ and
$R^5$, $R^6$, $R^7$ and $R^8$ are the same or different and mean hydrogen, $C_{1-6}$ alkyl, $CF_3$, nitro, halogen, cyano, $SO_pR^{11}$, $SO_2NR^{12}R^{13}$, $SO_3H$, $SO_3C_{1-6}$ alkyl, $OR^{14}$, optionally substituted aryl or hetaryl, whereby $R^2$ means hydrogen or $-(CH_2)_q-R^3$, means hydrogen, hydroxy, $C_{1-6}$ alkoxy or $NR^{15}R^{16}$, n, m and q each mean 0, 1, 2 or 3, Z means POXY, OPOXY, $SO_2R^{17}$, $CO_2R^{18}$, cyano or tetrazole, $R^{11}$ means H, $C_{1-6}$ alkyl, phenyl, p means 0, 1 or 2, $R^{12}$, $R^{13}$ and $R^{18}$ mean hydrogen or $C_{1-4}$ alkyl, $R^{14}$ means H, or $C_{1-6}$ alkyl optionally substituted in 1–3 places with halogen, $R^{17}$ means hydroxy, $C_{1-6}$ alkoxy or $NR^{19}R^{20}$, X and Y are the same or different and mean hydroxy, $C_{1-6}$ alkoxy, $C_{1-4}$ alkyl or $NR^{21}R^{22}$, $R^{15}$ and $R^{16}$, $R^{21}$ and $R^{22}$ are the same or different and mean hydrogen, $C_{1-4}$ alkyl, aryl, or together with the nitrogen atom form a saturated 5- to 7-membered heterocycle that can contain another oxygen, sulfur or nitrogen atom and can be substituted or form an unsaturated 5-membered heterocycle that can contain 1–3 N atoms and can be substituted, $R^{19}$ and $R^{20}$ are the same or different and mean hydrogen, $C_{1-4}$ alkyl, or together with the nitrogen atom form a saturated 5- to 7-membered heterocycle that can contain another oxygen, sulfur or nitrogen atom, as well as their isomers or salts, whereby at least one of substituents $R^5$, $R^6$, $R^7$ or $R^8$ means aryl or hetaryl.

The compounds of general formula I also contain the possible tautomeric forms and comprise the E or Z isomers or, if a chiral center is present, the racemates or enantiomers.

The substituents are preferably in 6- and/or 7-position.

Alkyl is defined respectively as a straight-chain or branched alkyl radical, such as, for example, methyl, ethyl, propyl, isopropyl, butyl, isobutyl, sec-butyl, pentyl, isopentyl, hexyl, whereby $C_{1-4}$ alkyl radicals are preferred.

Halogen is defined respectively as fluorine, chlorine, bromine and iodine.

Aryl radical $R^5$, $R^6$, $R^7$ or $R^8$ has 6–12 carbon atoms, such as naphthyl, biphenyl or especially phenyl and can be substituted in one or more places. Hetaryls are defined as optionally substituted 5- or 6-membered heteroatoms with 1–3 nitrogen, oxygen and/or sulfur atoms, which can contain a fused benzene ring, such as, for example, thiophene, furan, oxazole, thiazole or pyridine, pyrimidine, pyrazine, pyridazine, triazine, quinoline, isoquinoline.

As substituents, in each case halogen, $C_{1-4}$ alkoxy, nitro, trifluoromethyl, $C_{1-4}$ alkyl, $NR^{23}R^{24}$ or $SR^{25}$ can occur in 1 or more places, whereby the meaning of $NR^{23}R^{24}$ corresponds to radical $NR^{15}R^{16}$ and the meaning of $R^{25}$ corresponds to radical $R^{14}$. The heteroaromatic compound can be linked to the quinoxaline in any position, but not on an N atom.

If $R^{15}$ and $R^{16}$, $R^{21}$ and $R^{22}$ $R^{19}$ and $R^{20}$ together with the nitrogen atom form a saturated heterocycle, then, for example, piperidine, pyrrolidine, morpholine, thiomorpholine, hexahydroazepine or piperazine is meant.

If $R^{15}$ and $R^{16}$, $R^{21}$ and $R^{22}$ together with the nitrogen atom form an unsaturated heterocycle, then, for example, imidazole, pyrazole, pyrrole and triazole can be mentioned.

If an acid function is contained, the physiologically compatible salts of organic and inorganic bases are suitable as salts, such as, for example, the readily soluble alkali and alkaline-earth salts, as well as salts with N-methyl-glucamine, dimethyl-glucamine, ethyl-glucamine, lysine, 1,6-hexadiamine, ethanolamine, glucosamine, sarcosine, serinol, tris-hydroxy-methyl-amino-methane, aminopropanediol, Sovak base, 1-amino-2,3,4-butanetriol.

If a basic function is contained, the physiologically compatible salts of organic and inorganic acids are suitable, such as HCl, $H_2SO_4$, phosphoric acid, citric acid, tartaric acid, i.a.

Preferred are compounds of formula I with Z=-POXY, $CO_2R^{18}$, $SO_3H$ or tetrazole, which are substituted in 5- and/or 6-position with $CF_3$, nitro, halogen, $SO_pR^{11}$, $SO_2NR^{12}R^{13}$ and in 7- and/or 8-position by an optionally substituted aryl or hetaryl radical.

The compounds of formula I as well as their physiologically compatible salts can be used as pharmaceutical agents because of their affinity for the AMPA receptors. Because of their action profile, the compounds according to the invention are suitable for the treatment of diseases that are caused by hyperactivity of excitatory amino acids, such as, for example, glutamate or aspartate. Since the new compounds act as antagonists of excitatory amino acids and show a high specific affinity for the AMPA receptors, in which they displace the radiolabeled specific agonist (RS)a-amino-3-hydroxy-5-methyl-4-isoxazolepropionate (AMPA) from the AMPA receptors, they are especially suitable for the treatment of those diseases that are affected by the receptors of excitatory amino acids, especially the AMPA receptor.

According to the invention, the compounds can be used for the treatment of neurological and psychiatric disorders that are triggered by the overstimulation of the AMPA receptor. The neurological diseases that can be treated functionally and preventatively include, for example, neurodegenerative disorders, such as Parkinson's disease, Alzheimer's disease, Huntington chorea, amyotrophic lateral sclerosis and olivopontocerebellar degeneration. According to the invention, the compounds can be used for the prevention of postischemic cell destruction, cell destruction after cerebral trauma, in a stroke, hypoxia, anoxia and hypoglycemia and for the treatment of senile dementia, AIDS dementia, neurological symptoms that are linked with HIV infections, multiinfarct dementia as well as epilepsy and muscle spasms. The psychiatric diseases include anxiety conditions, schizophrenia, migraine, conditions of pain, as well as the treatment of sleep disorders and the withdrawal symptoms after drug abuse, such as in alcohol, cocaine, benzodiazepine or opiate withdrawal. In addition, the compounds can be used in the prevention of tolerance development during long-term treatment with sedative pharmaceutical agents, such as, for example, benzodiazepines, barbiturates and morphine. Moreover, the compounds can be used as anesthetic agents (anesthesia), anti-analgesics or anti-emetics.

For use of the compounds according to the invention as pharmaceutical agents, they are put in the form of a pharmaceutical preparation, that, besides the active ingredient for enteral or parenteral administration, contains suitable pharmaceutical, organic or inorganic inert vehicles, such as, for example, water, gelatin, gum arabic, lactose, starch, magnesium stearate, talc, vegetable oils, polyalkyleneglycols, etc. The pharmaceutical preparations can be in solid form, for example, as tablets, coated tablets, suppositories, capsules or in liquid form, for example, as solutions, suspensions or emulsions. Moreover, they optionally contain adjuvants, such as preservatives, stabilizers, wetting agents or emulsifiers, salts for changing the osmotic pressure or buffers.

Especially suitable for parenteral use are injection solutions or suspensions, in particular aqueous solutions of the active compounds in polyhydroxyethoxylated castor oil.

Surface-active adjuvants, such as salts of bile acids or animal or vegetable phospholipids, but also mixtures thereof as well as liposomes or their components can also be used as vehicle systems.

Especially suitable for oral use are tablets, coated tablets or capsules with talc and/or hydrocarbon vehicles or binders, such as, for example, lactose, corn or potato starch. The use can also be carried out in liquid form, such as, for example, as juice, to which a sweetener is optionally added.

The dosage of the active ingredients can vary depending on method of administration, age and weight of the patient, type and severity of the disease to be treated and similar factors. The daily dose is 0.5–1000 mg, preferably 50–200 mg, whereby the dose can be administered as a single dose to be administered once or subdivided into 2 or more daily doses.

The production of the compounds according to the invention is carried out according to methods known in the art. For example, compounds of formula I are attained in that a compound of formula II

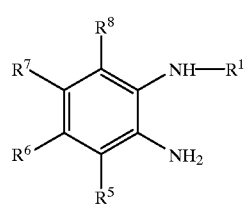

(II)

in which R' to $R^8$ have the above-mentioned meaning, is cyclized with oxalic acid or reactive oxalic acid derivatives, and optionally then the ester group is saponified or the acid group is esterified or amidated or a tetrazole group is introduced or the isomers are separated or the salts are formed.

Compounds of formula II are obtained, for example, by a leaving group being replaced by aryl or hetaryl in a compound of formula III

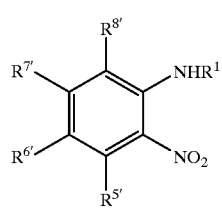

(III)

in which R' has the above-mentioned meaning and $R^{5'}$, $R^{6'}$, $R^{7'}$ and $R^{8'}$ mean a leaving group or $R^5$, $R^6$, $R^7$ or $R^8$, and then the nitro group being reduced in the usual way to an amino group.

The cyclization to compounds of formula I is carried out single-stage with oxalic acid in a known way in an acid environment or single-stage with a reactive oxalic acid derivative or else two-stage. Regarded as preferable is the two-stage process, in which the diamine is reacted with an oxalic acid derivative such as oxalic ester semi-chloride or reactive oxalic acid imidazole derivatives in polar solvents, such as cyclic or acyclic ethers or halogenated hydrocarbons, for example, tetrahydrofuran, diethyl ether or methylene chloride or else in water according to Schotten Baumann in the presence of a base such as organic amines, for example, triethylamine, pyridine, Hunig base or dimethylaminopyridine or else soda or sodium hydroxide solution. The subsequent cyclization can be performed in a basic or else acidic manner, but preferably in an acid environment, whereby solubilizer, such as alcohol or acetonitrile, can be added to the reaction mixture.

Alkali hydrides, such as NaH, which are used in inert solvents such as hydrocarbons or ethers, also represent suitable bases for the two-stage process.

As leaving groups in the production of compounds of formula II, halogens such as fluorine, chlorine, bromine, iodine or O-mesylate, O-tosylate, O-triflate or O-nonaflate are suitable. The nucleophilic substitution for introducing the aryl or hetaryl radicals is performed under catalysis of transition metal complexes such as Pd(O), e.g., tetrakis (triphenylphosphine) palladium or Pd(2+), e.g., palladium-bis-tri-o-tolylphosphine-dichloride or nickel (O) according to methods known in the literature optionally in the presence of a base and is fostered by an activating electron-attracting group, such as, e.g., nitro, cyano, trifluoromethyl, preferably in o-position.

As nucleophiles, for example, aryl or hetaryl boronic acids or boranes or tin-organic compounds, zinc-organic compounds or else Grignard compounds are suitable. The reaction can be performed 2in polar solvents such as dimethylformamide, dimethylacetamide, acetonitrile, in hydrocarbons such as toluene or in ethers such as tetrahydrofuran, dimethoxyethane or diethyl ether. As bases, inorganic bases, such as alkali or alkaline-earth hydroxides or -carbonates, or organic bases, such as cyclic, acyclic and aromatic amines, such as pyridine, triethylamine, DBU or Hunig base, are suitable.

The optionally subsequent saponification of an ester group can be carried out in a basic or preferably acidic manner, by hydrolyzing the reaction mixture at a higher temperature up to the boiling temperature in the presence of acids, such as highly concentrated aqueous hydrochloric acid optionally in solvents, such as, for example, trifluoroacetic acid or alcohols. Phosphonic acid esters are preferably hydrolyzed by heating in highly concentrated aqueous acids, such as, for example, concentrated hydrochloric acid optionally with the addition of an alcohol or by treatment with a trimethylsilyl halide in inert solvents, such as, e.g., acetonitrile and subsequent treatment with water.

The esterification of the carboxylic acid or phosphonic acid is carried out in a way known in the art with the corresponding alcohol optionally by acid catalysis or in the presence of an activated acid derivative. As activated acid derivatives, for example, acid chloride, acid imidazolide or acid anhydride are suitable. In phosphonic acids, the esterification can be achieved by reaction with orthoesters optionally by the addition of catalysts such as p-toluenesulfonic acid.

The amidation is carried out on the free acids or on their reactive derivatives, such as, for example, acid chlorides, mixed anhydrides, imidazolides or azides, by reaction with the corresponding amines at room temperature.

The introduction of the tetrazole is possible by reaction of the corresponding nitrile with an azide, such as, e.g., trimethylsilylazide, hydrazoic acid or sodium azide, optionally by the addition of a proton source, such as, e.g., ammonium chloride or triethylammonium chloride in polar solvents such as dimethylformamide, dimethylacetamide or N-methylpyrrolidone at temperatures of up to the boiling point of the solvent.

The mixtures of isomers can be separated into the enantiomers or E/Z isomers according to commonly used methods, such as, for example, crystallization, chromatography or salt formation.

The production of the salts is carried out in the usual way, by a solution of the compound of formula I being mixed with the equivalent amount or an excess of a base or acid, which optionally is in solution, and the precipitate being separated or the solution being worked up in the usual way.

If the production of the starting compounds is not described, they are known or can be produced analogously to known compounds, for example, according to WO93/08173, WO 94/25469 or can be produced according to processes described here.

The following examples are to explain the process according to the invention:

EXAMPLES

Production of Starting Materials

A.) 3.3 g (30 mmol) of aminomethanephosphonic acid is introduced into 120 ml of water and 120 ml of acetonitrile together with 3.37 g (31.8 mmol) of soda and mixed with 7.8 g (97%, 30 mmol) of 3-trifluoromethyl-4,6-dichloronitrobenzene and refluxed for 4 hours at a bath temperature of 120° C. After the acetonitrile is drawn off in a rotary evaporator, it is extracted three times with 100 ml of ethyl acetate. The organic phase is washed with a little water. It contains starting material and is discarded. The collected aqueous phase is made acidic at pH 1 with 4N hydrochloric acid and extracted three times with 100 ml of ethyl acetate each. The organic phase is washed with water, dried, filtered and concentrated by evaporation. 6.85 g (68% of theory) of N-(2-nitro-4-trifluoromethyl-5-chloro-phenyl)-aminomethanephosphonic acid with a melting point of 207.3° C. is obtained.

B.) 1.67 g of N-(2-nitro-4-trifluoromethyl-5-chloro-phenyl-aminomethanephosphonic acid is mixed in 25 ml of triethyl orthoformate with 190 mg of p-toluenesulfonic acid, and it is heated for 3 hours to a bath temperature of 150° C. After concentration by evaporation in a vacuum, it is taken up in 25 ml of water and extracted three times with 25 ml of ethyl acetate each. The collected ethyl acetate phase is washed once with water, dried, filtered and concentrated by evaporation.

2 g (>100% of theory) of N-(2-nitro-4-trifluoromethyl-5-chloro-phenyl)-aminomethanephosphonic acid diethyl ester is obtained.

Example 1

A.) 600 mg of N-(2-nitro-4-trifluoromethyl-5-chloro-phenyl)-aminomethanephosphonic acid diethyl ester is mixed in 36 ml of toluene with 9 ml of ethanol, 3.36 ml of 2M soda solution, 58 mg of tetrakis(triphenylphosphine) palladium and 204 mg of phenylboronic acid, and it is heated under argon for 4 hours to a bath temperature of 110° C. After concentration by evaporation, it is dispersed in ethyl acetate and water, and the ethyl acetate phase is dried, filtered and concentrated by evaporation. The residue is chromatographed twice on silica gel, first with the mobile solvent methylene chloride:ethanol=95:5 and then the correspondingly combined fractions first with cyclohexane for separation from triphenylphosphine and later with ethyl acetate. 218 mg (33% of theory) of N-(4-nitro-2-trifluoromethyl-biphen-5-yl)-aminomethanephosphonic acid diethyl ester is obtained.

Produced analogously are:

N-(2-Nitro-4-trifluoromethyl-5-(3-pyridyl)-phenyl)-aminomethanephosphonic acid diethyl ester N-(4-nitro-2-trifluoromethyl-4'-methoxybiphen-5-yl)-aminomethanephosphonic acid diethyl ester N-(4-nitro-2-trifluoromethyl-4'-dimethylaminobiphen-5-yl)-aminomethanephosphonic acid diethyl ester N-(4-nitro-2-trifluoromethyl-4'-thiomethylbiphen-5-yl)-aminomethanephosphonic acid diethyl ester N-(4-nitro-2-trifluoromethyl-4'-chlorobiphen-5-yl)-aminomethanephosphonic acid diethyl ester N-(4-nitro-2-trifluoromethyl-4'-fluorobiphen-5-yl)-aminomethanephosphonic acid diethyl ester N-(4-nitro-2-trifluoromethyl-4'-trifluoromethylbiphen-5-yl)-aminomethanephosphonic acid diethyl ester B.) 500 mg of N-(4-nitro-2-trifluoromethyl-biphen-5-yl)-aminomethanephosphonic acid diethyl ester is dissolved in 35 ml of methanol and added in drops to a suspension of 195 mg of iron powder in a solution of 300 mg of ammonium chloride in 15 ml of water. The batch is heated for 1 hour to a bath temperature of 80° C. After concentration by evaporation, it is dispersed in ethyl acetate/water. The ethyl acetate phase is concentrated by evaporation and chromatographed on silica gel with acetone:hexane=1:1 as an eluant. The combined fractions are stirred in ethanol with 1N hydrochloric acid at room temperature for 1 hour and concentrated by evaporation. 214 mg (60% of theory) of N-(4-amino-2-trifluoromethyl-biphen-5-yl)-aminomethanephosphonic acid diethyl ester is obtained.

Produced analogously are:

N-(2-Amino-4-trifluoromethyl-5-(3-pyridyl)-phenyl)-aminomethanephosphonic acid diethyl ester N-(4-amino-2-trifluoromethyl-4'-methoxybiphen-5-yl)-aminomethanephosphonic acid diethyl ester N-(4-amino-2-trifluoromethyl-4'-dimethylaminobiphen-5-yl)-aminomethanephosphonic acid diethyl ester N-(4-amino-2-trifluoromethyl-4'-thiomethylbiphen-5-yl)-aminomethanephosphonic acid diethyl ester N-(4-amino-2-trifluoromethyl-4'-chlorobiphen-5-yl)-aminomethanephosphonic acid diethyl ester N-(4-amino-2-trifluoromethyl-4'-fluorobiphen-5-yl)-aminomethanephosphonic acid diethyl ester N-(4-amino-2-trifluoromethyl-4'-trifluoromethylbiphen-5-yl)-aminomethanephosphonic acid diethyl ester C.) 416 mg of N-(4-amino-2-trifluoromethyl-biphen-5-yl)-aminomethanephosphonic acid diethyl ester is dissolved in 25 ml of absolute tetrahydrofuran and mixed with 0.35 g of triethylamine. A solution of 0.37 g of oxalic acid ethyl ester chloride in 12 ml of absolute tetrahydrofuran is added in drops to this solution at room temperature. After the addition is completed, it is stirred for another 4 hours at room temperature. Precipitate is suctioned off, and the filtrate is concentrated by evaporation. The residue is taken up in 30 ml of 1N hydrochloric acid and 30 ml of ethanol, and it is stirred for 2 hours at a bath temperature of 120° C. After concentration by evaporation, the residue is chromatographed on silica gel with dichloromethane:ethanol=10:1. 320 mg (60% of theory) of [(6-trifluoromethyl-7-phenyl-1,2,3,4-tetrahydroquinoxaline-2,3-dion)-1yl]-methanephosphonic acid diethyl ester is obtained.

Produced analogously are:

N-[(6-Trifluoromethyl-7-(pyrid-3-yl)-1,2,3,4-tetrahydroquinoxaline-2,3-dion)-1yl]-methanephosphonic acid diethyl ester.

N-[(6-Trifluoromethyl-7-(4-methoxyphenyl)-1,2,3,4-tetrahydroquinoxaline-2,3-dion)-1yl]-methanephosphonic acid diethyl ester.

N-[(6-Trifluoromethyl-7-(4-dimethylaminophenyl)-1,2,3,4-tetrahydroquinoxaline-2,3-dion)-1yl]-methanephosphonic acid diethyl ester.

N-[(6-Trifluoromethyl-7-(4-thiomethylphenyl)-1,2,3,4-tetrahydroquinoxaline-2,3-dion)-1yl]-methanephosphonic acid diethyl ester.

N-[(6-Trifluoromethyl-7-(4-chlorophenyl)-1,2,3,4-tetrahydroquinoxaline-2,3-dion)-1yl] -methanephosphonic acid diethyl ester.

N-[(6-Trifluoromethyl-7-(4-fluorophenyl)-1,2,3,4-tetrahydroquinoxaline-2,3-dion)-1yl]-methanephosphonic acid diethyl ester.

N-[(6-Trifluoromethyl-7-(4-trifluoromethylphenyl)-1,2,3,4-tetrahydroquinoxaline-2,3-dion)-1yl]-methanephosphonic acid diethyl ester.

Example 2

148 mg of [(6-trifluoromethyl-7-phenyl-1,2,3,4-tetrahydroquinoxaline-2,3-dion)-1yl]-methanephosphonic acid diethyl ester is heated in 4 ml of concentrated hydrochloric acid for 2 hours to a bath temperature of 120° C. After concentration by evaporation in a vacuum, it is dried on potassium hydroxide in a vacuum. 134 mg of [(6-trifluoromethyl-7-phenyl-1,2,3,4-tetrahydroquinoxaline-2,3-dion)-1yl]-methanephosphonic acid is obtained.

Produced analogously are:

N-[(6-Trifluoromethyl-7-(pyrid-3-yl)-1,2,3,4-tetrahydroquinoxaline-2,3-dion)-1yl]-methanephosphonic acid.

N-[(6-Trifluoromethyl-7-(4-methoxyphenyl)-1,2,3,4-tetrahydroquinoxaline-2,3-dion)-1yl]-methanephosphonic acid.

N-[(6-Trifluoromethyl-7-(4-dimethylaminophenyl)-1,2,3,4-tetrahydroquinoxaline-2,3-dion)-1yl])-methanephosphonic acid.

N-[(6-Trifluoromethyl-7-(4-thiomethylphenyl)-1,2,3,4-tetrahydroquinoxaline-2,3-dion)-1yl]-methanephosphonic acid.

N-[(6-Trifluoromethyl-7-(4-chlorophenyl)-1,2,3,4-tetrahydroquinoxaline-2,3-dion)-1yl]-methanephosphonic acid.

N-[(6-Trifluoromethyl-7-(4-fluorophenyl)-1,2,3,4-tetrahydroquinoxaline-2,3-dion)-1yl]-methanephosphonic acid.

N-[(6-Trifluoromethyl-7-(4-trifluoromethylphenyl)-1,2,3,4-tetrahydroquinoxaline-2,3-dion)-1yl]-methanephosphonic acid.

What is claimed is:

1. Compounds of formula I (I)

in which $R^1$ means $—(CH_2)_n—CR^2H—(CH_2)_m—Z$ and $R^5$, $R^6$, $R^7$ and $R^8$ are the same or different and mean hydrogen, $C_{1-6}$ alkyl, $CF_3$, nitro, halogen, cyano, $SO_pR^{11}$, $SO_2NR^{12}R^{13}$, $SO_3H$, $SO_3C_{1-6}$ alkyl, $OR^{14}$, phenyl, pyridyl or substituted phenyl having a substituent selected from the group consisting of $C_{1-4}$-alkyl, $C_{1-4}$-alkoxy, nitro, trifluoromethyl, $NR^{15}R^{16}$, and $SR^{14}$, whereby $R^2$ means hydrogen or $—(CH_2)_q—R^3$, $R^3$ means hydrogen, hydroxy, $C_{1-6}$ alkoxy or $NR^5R^{16}$, n, m and q each mean 0, 1, 2 or 3, Z means POXY, OPOXY, $SO_2R^{17}$, $CO_2R^{18}$, cyano or tetrazole, $R^{11}$ means H, $C_{1-6}$ alkyl, phenyl, p means 0, 1 or 2, $R^{12}$, $R^{13}$ and $R^{18}$ mean hydrogen or $C_{1-4}$ alkyl, $R^{14}$ means H, unsubstituted $C_{1-6}$ alkyl or $C_{1-6}$ alkyl substituted in 1–3 places with halogen, $R^{17}$ means hydroxy, $C_{1-6}$ alkoxy or $NR^{19}R^{20}$, X and Y are the same or different and mean hydroxy, $C_{1-6}$ alkoxy, $C_{1-4}$ alkyl or $NR^{21}R^{22}$, $R^{15}$ and $R^{16}$ are the same or different and mean hydrogen, $C_{1-4}$ alkyl or aryl, $R^{21}$ and $R^{22}$ are the same or different and mean hydrogen, $C_{1-4}$ alkyl or aryl, $R^{19}$ and $R^{20}$ are the same or different and mean hydrogen or $C_{1-4}$ alkyl, as well as their isomers or salts, wherein a) at least one of substituents $R^5$, $R^6$, $R^7$ or $R^8$ is phenyl or pyridyl which is not linked to the quinoxaline moiety via a nitrogen atom and b) Z is not $CO_2R^{18}$ where $R^5$, $R^6$, $R^7$ or $R^8$ is phenyl.

2. [(6-Trifluoromethyl-7-phenyl-1,2,3,4-tetrahydroquinoxaline-2,3-dion)-1-yl]-methanephosphonic acid diethyl ester.

3. Pharmaceutical agent that contains a compound according to claim 1 and a pharmaceutical organic or inorganic inert vehicle.

4. Process for the production of the compounds according to claim 1, characterized in that a compound of formula II (II)

in which $R^1$ and $R^5$ to $R^8$ have the meaning as defined in claim 1, is cyclized with oxalic acid or reactive oxalic acid derivatives.

* * * * *

UNITED STATES PATENT AND TRADEMARK OFFICE
CERTIFICATE OF CORRECTION

PATENT NO.    : 6,143,733
DATED         : November 7, 2000
INVENTOR(S)   : Andreas Huth, Martin Kruger, Eckhard Ottow, Dieter Scidelmann, Graham H. Jones, Herbert Schneider and Lechoslaw Turski It is certified that error appears in the above-identified patent and that said Letters Patent is hereby corrected as shown below:

<u>Column 8,</u>
Line 13, reads "$NR^5R^{16}$" when it should read -- $NR^{15}R^{16}$ --.

Signed and Sealed this

Thirtieth Day of April, 2002

*Attest:*

JAMES E. ROGAN
*Attesting Officer*   *Director of the United States Patent and Trademark Office*